(12) United States Patent
Ishiyama et al.

(10) Patent No.: US 10,349,507 B2
(45) Date of Patent: Jul. 9, 2019

(54) MEDICAL APPARATUS AND X-RAY HIGH VOLTAGE APPARATUS

(71) Applicant: TOSHIBA MEDICAL SYSTEMS CORPORATION, Otawara-Shi (JP)

(72) Inventors: Fumio Ishiyama, Nasushiobara (JP); Kenji Hirohata, Minato-Ku (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 1022 days.

(21) Appl. No.: 14/263,173

(22) Filed: Apr. 28, 2014

(65) Prior Publication Data

US 2014/0233708 A1    Aug. 21, 2014

Related U.S. Application Data

(63) Continuation of application No. PCT/JP2013/073834, filed on Sep. 4, 2013.

(30) Foreign Application Priority Data

Sep. 11, 2012    (JP) ................... 2012-199659

(51) Int. Cl.
*H02H 5/04*    (2006.01)
*G01K 1/12*    (2006.01)
(Continued)

(52) U.S. Cl.
CPC ............. *H05G 1/54* (2013.01); *A61B 6/03* (2013.01); *A61B 6/4488* (2013.01); *A61B 6/56* (2013.01);
(Continued)

(58) Field of Classification Search
None
See application file for complete search history.

(56) References Cited

U.S. PATENT DOCUMENTS 3,362,217 A * 1/1968 Rush .................. G01K 3/04
374/E3.004
5,107,447 A * 4/1992 Ozawa ............... G01R 15/142
324/536
(Continued)

FOREIGN PATENT DOCUMENTS

JP    03-261877 A    11/1991
JP    07-014948 A    1/1995
(Continued)

OTHER PUBLICATIONS

Pang et al., "Life prediction scheme for electrolytic capacitors in power converts without current sensor", 25th Annual IEEE APEC, 2010, p. 973-979.*
(Continued)

*Primary Examiner* — Mohamed Charioui
*Assistant Examiner* — Catherine T. Rastovski
(74) *Attorney, Agent, or Firm* — Oblon, McClelland, Maier & Neustadt, L.L.P.

(57) ABSTRACT

A medical apparatus includes a power device, a temperature sensor, a conversion processing unit and a prediction time period calculation unit. The temperature sensor detects temperature data. The conversion processing unit refers to temperature data obtained by the temperature sensor in a table in which at least one of temperature data for inside a case covering the power device and temperature data for a wire bonded to the power device is associated with data of actually measured temperatures, and obtains at least one of the temperature data for inside the case and the temperature data for the wire. The prediction time period calculation unit calculates a prediction time period until a failure of the power device based on the obtained temperature data.

10 Claims, 9 Drawing Sheets

(51) Int. Cl.
  G07C 3/00    (2006.01)
  G06F 17/40   (2006.01)
  G06F 19/00   (2011.01)
  H05G 1/54    (2006.01)
  H01L 23/34   (2006.01)
  H01L 23/00   (2006.01)
  A61B 6/03    (2006.01)
  A61B 6/00    (2006.01)
  H05G 1/10    (2006.01)
  G08B 21/18   (2006.01)
  H01L 25/07   (2006.01)
  G16H 40/40   (2018.01)

(52) U.S. Cl.
  CPC .............. *H01L 23/34* (2013.01); *H01L 24/48* (2013.01); *H05G 1/10* (2013.01); *G01K 1/12* (2013.01); *G06F 17/40* (2013.01); *G06F 19/00* (2013.01); *G07C 3/00* (2013.01); *G08B 21/182* (2013.01); *G16H 40/40* (2018.01); *H01L 24/06* (2013.01); *H01L 24/32* (2013.01); *H01L 24/49* (2013.01); *H01L 24/73* (2013.01); *H01L 25/072* (2013.01); *H01L 2224/04042* (2013.01); *H01L 2224/06155* (2013.01); *H01L 2224/32225* (2013.01); *H01L 2224/48091* (2013.01); *H01L 2224/48465* (2013.01); *H01L 2224/49175* (2013.01); *H01L 2224/73265* (2013.01); *H01L 2924/00014* (2013.01); *H01L 2924/1203* (2013.01); *H01L 2924/1301* (2013.01); *H01L 2924/1302* (2013.01); *H01L 2924/1305* (2013.01); *H01L 2924/1306* (2013.01); *H01L 2924/13033* (2013.01); *H01L 2924/13055* (2013.01); *H01L 2924/13091* (2013.01); *H01L 2924/30107* (2013.01); *H01L 2924/3512* (2013.01); *H02H 5/04* (2013.01)

(56) References Cited

U.S. PATENT DOCUMENTS

| | | | | |
|---|---|---|---|---|
| 5,214,595 | A | * | 5/1993 | Ozawa ................ G01R 15/142 324/536 |
| 2005/0071090 | A1 | | 3/2005 | Katou |
| 2010/0100337 | A1 | * | 4/2010 | Vichare ................ G06F 11/008 702/34 |
| 2010/0250149 | A1 | * | 9/2010 | Omori ................ G01R 31/2849 702/34 |
| 2012/0219035 | A1 | * | 8/2012 | Kwon ................... G01K 7/021 374/170 |
| 2013/0257051 | A1 | * | 10/2013 | Spruce .................. F03D 7/028 290/44 |

FOREIGN PATENT DOCUMENTS

| | | | |
|---|---|---|---|
| JP | 08-126337 | A | 5/1996 |
| JP | 2005-259486 | A | 9/2005 |
| JP | 2005-354812 | A | 12/2005 |
| JP | 2006-067690 | A | 3/2006 |
| JP | 2007-207585 | A | 8/2007 |
| JP | 2007207585 | * | 8/2007 |
| JP | 2008-241432 | A | 10/2008 |
| JP | 2010-056333 | A | 3/2010 |
| JP | 2011-023569 | A | 2/2011 |
| WO | WO 2004/082114 | A1 | 9/2004 |

OTHER PUBLICATIONS

International Search Report issued on Oct. 1, 2013 for PCT/JP2013/073834 filed on Sep. 4, 2013 with English translation.
International Preliminary Report on Patentability and Written Opinion issued Mar. 17, 2015 in PCT/JP2013/073834 (submitting English translation only).

* cited by examiner

MEDICAL APPARATUS AND X-RAY HIGH VOLTAGE APPARATUS

CROSS-REFERENCE TO RELATED APPLICATION

This application is a Continuation Application of No. PCT/JP2013/73834, filed on Sep. 4, 2013, and the PCT application is based upon and claims the benefit of priority from Japanese Patent Application No. 2012-199659, filed on Sep. 11, 2012, the entire contents of which are incorporated herein by reference.

FIELD

The present embodiment as one aspect of the present invention relates to a medical apparatus and an X-ray high voltage apparatus that include a power device.

BACKGROUND

In a medical image diagnosis apparatus such as an X-ray CT (computed tomography) apparatus or an X-ray apparatus, a high-power power device (semiconductor device directed at electric power unit) is included in a converter and an inverter of an X-ray high voltage apparatus in order to generate a high voltage to be supplied to an X-ray tube. When the medical image diagnosis apparatus is operating, the power devices of the X-ray high voltage apparatus undergo a rapid increase in temperature each time that X-rays are generated.

The output power of the X-ray high voltage apparatus is a large amount of several tens of kilowatts to hundreds of kilowatts. Consequently, an IGBT (insulated gate bipolar transistor) module or an MOSFET (metal-oxide-semiconductor field-effect transistor) module or the like is often used as a power device of a converter and an inverter in the X-ray high voltage apparatus.

As a conventional X-ray high voltage apparatus, an apparatus is known in which a converter is formed so as to realize a stable power factor even if an input AC power supply voltage fluctuates.

However, according to the conventional technology, in a medical image diagnosis apparatus such as an X-ray CT apparatus or an X-ray apparatus, the accumulation of damage to a power device provided in a converter or an inverter of an X-ray high voltage apparatus or to a bonding wire joined thereto is one of the main causes of a failure of the X-ray high voltage apparatus. Consequently, there is a problem that if such a failure suddenly occurs during a radiography operation, image data based on the radiography operation is wasted and it is necessary to re-perform the radiography operation.

It is known that damage to a power device is due to strain caused by expansion and contraction of an internal component member that is caused by temperature amplitudes. However, in the case of a medical image diagnosis apparatus, the number of CT scans and the number of X-ray radiographs vary depending on the conditions of use such as the diagnostic purpose and the physique of the patient, and temperature amplitudes of the power devices or bonding wires vary significantly. Hence, a heat cycle life or a power cycle life of a power device cannot be determined based on a constant temperature amplitude, and heretofore it has been difficult to assess the degree of damage to a power device or to predict the amount of damage thereto.

BRIEF DESCRIPTION OF THE DRAWINGS

In accompanying drawings.

DETAILED DESCRIPTION

A medical apparatus and an X-ray high voltage apparatus according to a present embodiment will now be described with reference to the accompanying drawings.

To solve the above-described problems, the present embodiments provide the medical apparatus, including: a power device; a temperature sensor configured to detect temperature data; a conversion processing unit configured to refer to temperature data obtained by the temperature sensor in a table in which at least one of temperature data for inside a case covering the power device and temperature data for a wire bonded to the power device is associated with data of actually measured temperatures, and obtain at least one of the temperature data for inside the case and the temperature data for the wire; and a prediction time period calculation unit configured to calculate a prediction time period until a failure of the power device based on the obtained temperature data.

To solve the above-described problems, the present embodiments provide the X-ray high voltage apparatus, including: a power device; a temperature sensor configured to detect temperature data; a conversion processing unit configured to refer to temperature data obtained by the temperature sensor in a table in which at least one of temperature data for inside a case covering the power device and temperature data for a wire bonded to the power device is associated with data of actually measured temperatures, and obtain at least one of the temperature data for inside the case and the temperature data for the wire; and a prediction time period calculation unit configured to calculate a prediction time period until a failure of the power device based on the obtained temperature data.

According to the medical apparatus and the X-ray high voltage apparatus according to the present embodiment, the life of a power device can be predicted from the viewpoint of a heat cycle life or a power cycle life. According to the medical apparatus and an X-ray high voltage apparatus according to the present embodiment, since a situation in which a failure of a power device suddenly occurs during a radiography operation can be avoided by predicting the life of the power device, it is not necessary to re-perform a radiography operation, and therefore unnecessary radiation exposure of a patient can be avoided.

The medical apparatus according to the present embodiment is an apparatus in which a power device is provided in a power supply circuit or the like. More specifically, the medical apparatus according to the present embodiment includes a therapy apparatus such as a radiation therapy apparatus, and a medical image diagnosis apparatus such as an MRI (magnetic resonance imaging) apparatus, an X-ray apparatus, or an X-ray CT apparatus. In a case where the medical apparatus is a radiation therapy apparatus, a power device is provided in a power supply circuit for generating radiation. Further, in a case where the medical apparatus is an MRI apparatus, a power device is provided in a power supply circuit for generating a gradient magnetic field or a power supply circuit for generating a high frequency pulse. In addition, when the medical apparatus is an X-ray apparatus or an X-ray CT apparatus, a power device is provided in a power supply circuit for generating X-rays (X-ray high voltage apparatus). Although an example is described hereunder in which an X-ray CT apparatus is used as a medical apparatus according to the present embodiment, the present invention is not limited thereto. It is sufficient that the medical apparatus 1 is an apparatus that includes a power device.

Note that various types of apparatus are available with respect to the X-ray CT apparatus as the medical apparatus according to the present embodiment, such as a rotate/rotate type in which an X-ray tube and a detector rotate as one body around an object, and a stationary/rotate type in which multiple detection elements are arrayed in a ring shape and only an X-ray tube rotates around an object, and the present invention is applicable to each type. The present embodiment is described taking the rotate/rotate type that is currently in mainstream use as an example.

Figure 1:
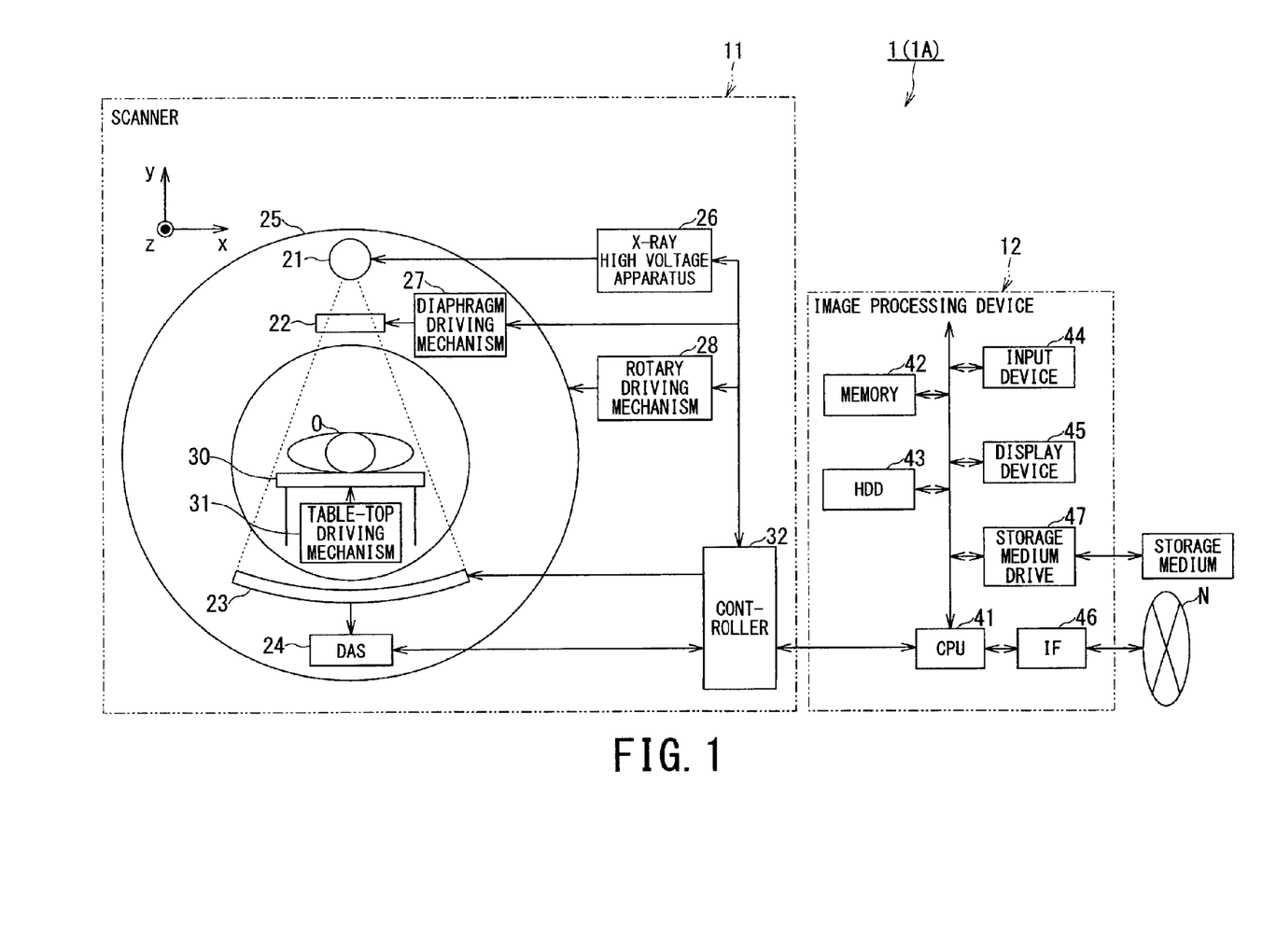
FIG. 1 is a diagram showing a configuration example of an X-ray CT apparatus as a medical apparatus according to a present embodiment.

FIG. 1 is a diagram showing a configuration example of an X-ray CT apparatus as a medical apparatus according to the present embodiment.

FIG. 1 illustrates an X-ray CT apparatus 1A as the medical apparatus 1 according to the present embodiment. The X-ray CT apparatus 1A is mainly constituted by a scanner 11 and an image processing device (console) 12. The scanner 11 of the X-ray CT apparatus 1A is normally installed in an examination room, and is configured to generate X-ray transmission data relating to a patient O (object). On the other hand, the image processing device 12 is normally installed in a control room that adjoins the examination room, and is configured to generate projection data based on the transmission data and generate and display a reconstructed image.

The scanner 11 of the X-ray CT apparatus 1A includes an X-ray tube 21, a diaphragm 22, an X-ray detector 23, a DAS (data acquisition system) 24, a rotary portion 25, an X-ray high voltage apparatus 26, a diaphragm driving mechanism 27, a rotary driving mechanism 28, a table-top 30, a table-top driving mechanism 31, and a controller 32.

The X-ray tube 21 generates X-rays by causing electron beams to collide against a metal target in accordance with a tube voltage supplied from the X-ray high voltage apparatus 26, and irradiates the X-rays towards the X-ray detector 23. Fan-beam X-rays or cone-beam X-rays are formed by the X-rays irradiated from the X-ray tube 21. Electric power required for irradiation of X-rays is supplied to the X-ray tube 21 through the X-ray high voltage apparatus 26 under the control of the controller 32.

The diaphragm 22 adjusts the irradiation range in a slice direction (z-axis direction) of the X-rays irradiated from the X-ray tube 21 by the diaphragm driving mechanism 27. That is, an X-ray irradiation range in the slice direction can be changed by adjusting an aperture of the diaphragm 22 by means of the diaphragm driving mechanism 27.

The X-ray detector 23 is a one-dimensional array detector having a plurality of detection elements in a channel direction and a single detection element in a row (slice) direction. Alternatively, the X-ray detector 23 is a two-dimensional array detector (also referred to as a "multi-slice detector") that has a matrix shape, that is, has a plurality of detection elements in a channel direction and a plurality of detection elements in a slice direction. The X-ray detector 23 detects X-rays that were irradiated from the X-ray tube 21 and transmitted through the patient O.

The DAS 24 amplifies signals of transmission data detected by each of the detection elements of the X-ray detector 23 and converts the signals to digital signals. Data output from the DAS 24 is supplied to the image processing device 12 via the controller 32 of the scanner 11.

The rotary portion 25 holds the X-ray tube 21, the diaphragm 22, the X-ray detector 23, the DAS 24 and the diaphragm driving mechanism 28 as a single unit. The rotary portion 25 is configured to be capable of rotating the X-ray tube 21, the diaphragm 22, the X-ray detector 23, the DAS 24 and the diaphragm driving mechanism 28 around the patient O as a single unit, in a state in which the X-ray tube 21 and the X-ray detector 23 face each other. The X-ray high voltage apparatus 27 may also be held by the rotary portion 25. Note that in the following description a direction parallel to the rotation central axis of the rotary portion 25 is defined as a z-axis direction, and a plane orthogonal to the z-axis direction is defined as an x-axis direction and a y-axis direction.

Under the control of the controller 32, the X-ray high voltage apparatus 26 supplies the X-ray tube 21 with electric power that is required to irradiate X-rays.

Figure 2:
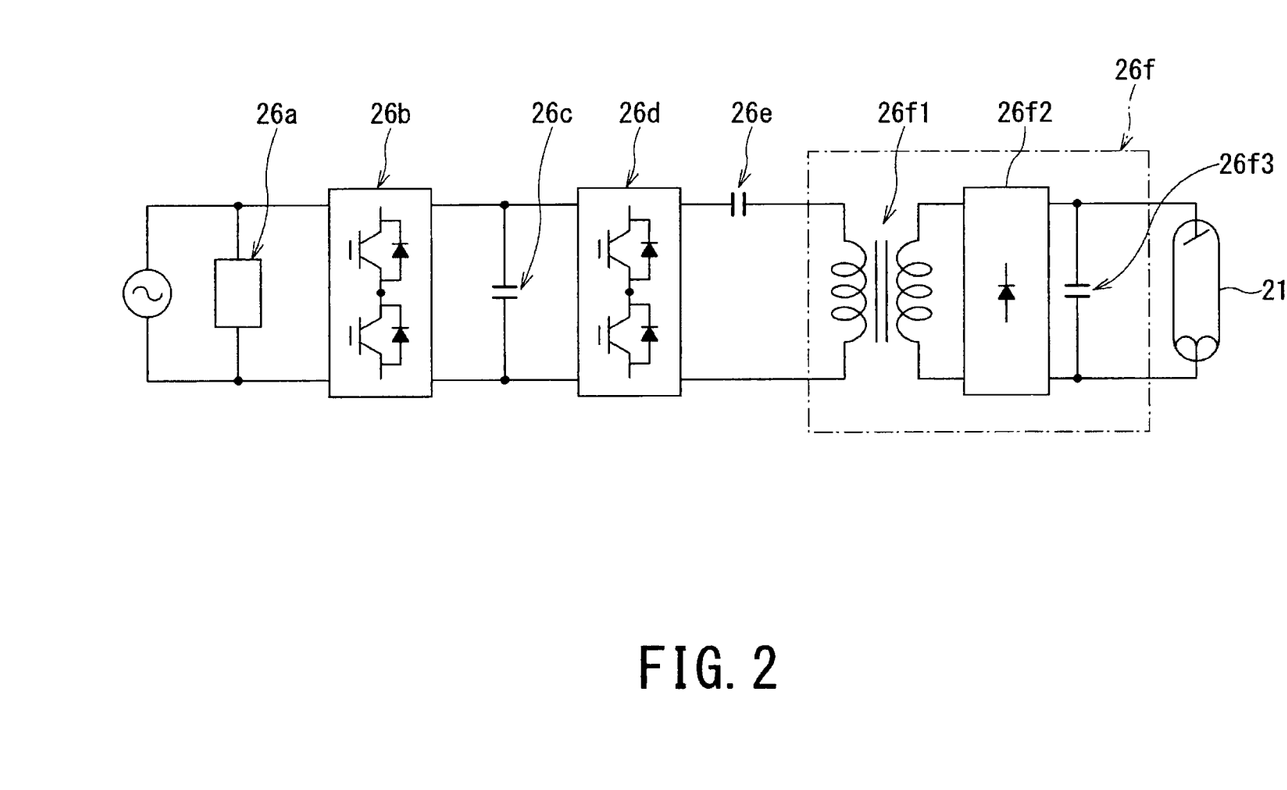
FIG. 2 is a schematic diagram showing a configuration example of an X-ray high voltage apparatus provided in the X-ray CT apparatus.

FIG. 2 is a schematic diagram showing a configuration example of the X-ray high voltage apparatus 26 provided in the X-ray CT apparatus 1A.

As shown in FIG. 2, the X-ray high voltage apparatus 26 is connected to a power supply (single-phase 200 V commercial power supply), and includes a voltage detection unit 26a, a converter 26b, a capacitor 26c, an inverter 26d, a capacitor 26e, and a high voltage generator 26f.

The X-ray high voltage apparatus 26 converts the power supply voltage to a direct current at the converter 26b, performs power control of the direct-current output from the converter 26b at the inverter 26d, transforms the current to a high voltage and rectifies the current at the high voltage generator 26f, and applies a high voltage to the X-ray tube 21. The direct current control of the converter 26b and the power control of the alternating current output at the inverter 26d are performed, for example, according to a PWM (pulse width modulation) method, and a target value thereof is received from a control circuit that is not shown in the drawings.

The high voltage generator 26f includes a step-up transformer 26f1, a rectifier circuit 26f2, and a capacitor 26f3. The voltage is boosted at the step-up transformer 26f1, and is rectified at the rectifier circuit 26f2. The capacitor 26f3 is used to smooth the output voltage.

The capacitor 26c stabilizes the output voltage of the converter 26b. The capacitor 26e is used for resonance, and is caused to resonate with the leakage inductance of the step-up transformer 26f1.

Figure 3:
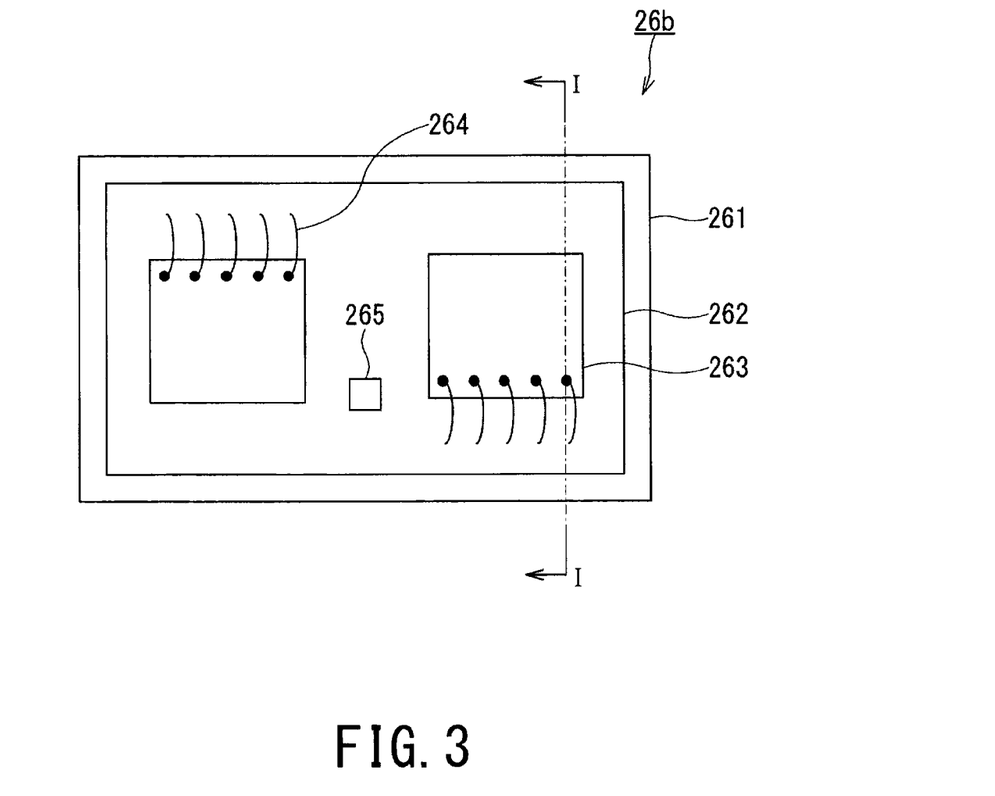
FIG. 3 is a schematic diagram showing a constructional example of a power device inside an inverter shown in FIG. 2.
Figure 4:
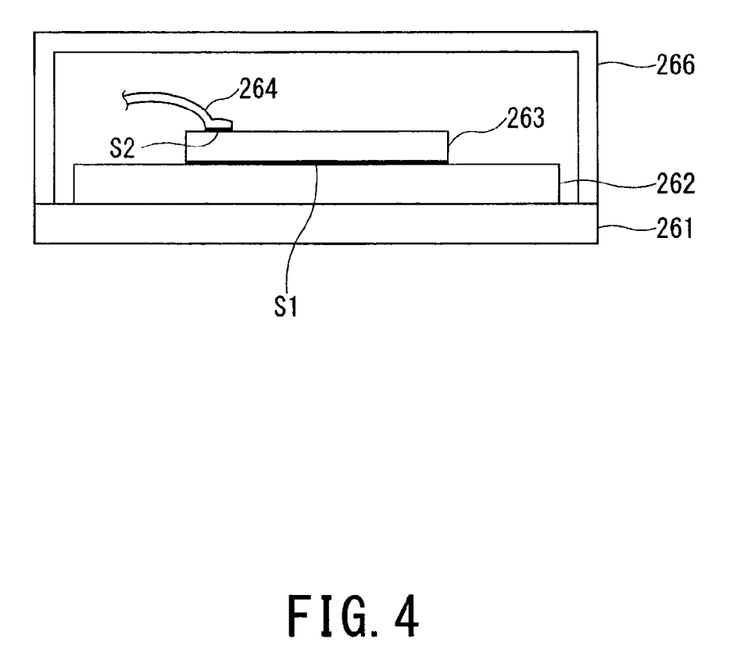
FIG. 4 is a schematic diagram showing a cross section along a line I-I shown in FIG. 3.

FIG. 3 is a schematic diagram showing a constructional example of a power device inside the inverter 26d (or converter 26b) shown in FIG. 2. FIG. 4 is a schematic diagram showing a cross section along a line I-I shown in FIG. 3.

As shown in FIG. 3 and FIG. 4, the X-ray high voltage apparatus 26 includes a heat sink 261, a substrate (a copper pattern, an insulated substrate, a conductor layer or the like) 262, a power device 263, a bonding wire (hereunder, referred to simply as "wire") 264 and a temperature sensor 265. A resin case (hereunder, referred to simply as "case") 266 is joined to the heat sink 261 so as to cover the power device 263, the wire 264 and the temperature sensor 265.

The substrate 262 is soldered onto the heat sink 261. A chip of the power device 263 is soldered onto the substrate 262 at a joint portion S1. The wire 264 is soldered onto the power device 263 at a joint portion S2.

In the power device 263, a series circuit is formed of a resistor and a thermistor, with the resistor being connected to a power supply, and the thermistor being grounded. The power device 263 is, for example, an IGBT (insulated gate bipolar transistor) module as a power transistor. Note that the power device 263 is not limited to an IGBT module. The power device 263 may also be, for example, a rectifier diode, a power MOSFET (metal-oxide-semiconductor field-effect transistor), a thyristor, a GTO (gate turn-off thyristor) or a triac or the like.

In this case, with respect to the relationship between temperature amplitudes and the life of the power device 263, a heat cycle life that causes cracking at the solder joint portion S1 between the substrate 262 and the chip of the power device 263 and the like and a power cycle life that causes cracking at the joint portion S2 between the power device 263 and the wire 264 and the like caused by momentary large currents are known that are due to temperature amplitudes of the entire power device 263 (inside the case 266 covering the power device 263). The heat cycle life is dominant in the case of scanning by the X-ray CT apparatus 1A or relatively continuous X-ray irradiation such as radioscopy performed by an X-ray apparatus (not shown in the drawings). In contrast, the power cycle life is dominant in the case of a flash X-ray irradiation such as radiography performed by an X-ray apparatus (not shown in the drawings).

However, the relationship between temperature amplitudes and the life is a relationship that applies to a case where generation of a fixed amount of heat is monotonously repeated at fixed time intervals. In contrast, in the case of the medical apparatus 1 such as the X-ray CT apparatus 1A or an X-ray apparatus (not shown in the drawings), it is difficult to assess the life of the power device 263 based on the number of CT scans or the number of X-ray radiographs since the conditions of use differ greatly depending on the diagnostic purpose and the physique of the patient. Therefore, in the present embodiment, the heat cycle life and the power cycle life are estimated by converting a sensor temperature of the temperature sensor 265 while the medical apparatus 1 is being used into a case temperature for inside of the case 266 and a temperature of the wire 264.

The temperature sensor 265 measures temperature data by sensing the temperature. A thermistor may be mentioned as an example of the temperature sensor 265. The temperature sensor 265 may be incorporated into the power device 263, or as shown in FIG. 3, may be provided outside the power device 263 at a position in the vicinity of the power device 263.

Note that since changes in temperature that are based on temperature data measured by the temperature sensor 265 during X-ray irradiation and immediately after X-ray irradiation ends are large, time series changes in the temperature can be accurately collected by setting a time interval at which to acquire the sensor temperature to a short period. On the other hand, since temperature changes are small at times other than during and immediately after X-ray irradiation, a time interval at which to collect the temperature data may be set to a long period in such cases. Further, by recording a X-ray irradiation start time and a time at which collection of temperature data ends that is a time after X-ray irradiation has ended and the temperature has dropped and is stable, it is possible to also cease collecting temperature data during a period in which the X-ray high voltage apparatus 26 is not operating. According to this method, changes in the sensor temperature over a long time period can be stored in a storage 268 using a small storage capacity while collecting detailed data regarding the sensor temperature during X-ray irradiation.

Returning to the description in FIG. 1, the diaphragm driving mechanism 27 has a mechanism that adjusts an irradiated range in the slice direction of X-rays on the diaphragm 22 under the control of the controller 32.

The rotary driving mechanism 28 has a mechanism that rotates the rotary portion 25 under the control of the controller 32 so that the rotary portion 25 rotates around a hollow portion in a state in which the relative positional relationship therebetween is maintained.

The patient O can be laid on the table-top 30.

The table-top driving mechanism 31 has a mechanism that moves the table-top 30 up and down along the y-axis direction as well as forward and rearward along the z-axis direction under the control of the controller 32. The rotary portion 25 includes an opening portion at a center portion thereof, and the patient O that has been laid on the table-top 30 is inserted into the opening portion.

The controller 32 has a CPU (central processing unit) and a memory and the like that are not shown in the drawings. The controller 32 executes scanning by controlling the X-ray detector 23, the DAS 24, the X-ray high voltage apparatus 26, the diaphragm driving mechanism 27, the rotary driving mechanism 28 and the table-top driving mechanism 31 and the like in accordance with an instruction from the image processing device 12.

The image processing device 12 of the X-ray CT apparatus 1A has a computer-based structure, and is capable of intercommunication with a network N (local area network). The image processing device 12 is mainly constituted by basic hardware such as a CPU 41, a memory 42, a HDD (hard disc drive) 43, an input device 44, a display device 45 and an IF (interface) 46. The CPU 41 is interconnected with each of the hardware components constituting the image processing device 12 via a bus as a common signal transmission line. The image processing device 12 may also include a storage medium drive 47.

The CPU 41 is a control apparatus having an integrated circuit (LSI) structure in which an electronic circuit made of semiconductors is enclosed in a package that has a plurality of terminals. When an instruction is input by an operator such as a physician by operating the input device 44 or the like, the CPU 41 executes a program stored in the memory 42. Alternatively, the CPU 41 loads to the memory 42 a program stored in the HDD 43, a program transferred from the network N and installed in the HDD 43, or a program read from a recording medium mounted in the storage medium drive 47 and installed in the HDD 43, and then executes the loaded program.

The memory 42 is a storage that includes a ROM (read only memory), a RAM (random access memory) or the like.

The memory 42 stores an IPL (initial program loading) program, a BIOS (basic input/output system) and data, and is used as a work memory of the CPU 41 or for temporarily storing data.

The HDD 43 is a storage having a configuration in which a metal disk on which magnetic material has been coated or vapor-deposited is undetachably incorporated. The HDD 43 stores programs (also including an OS (operating system) in addition to application programs and the like) that are installed in the image processing device 12 as well as data. The OS can also be caused to provide a GUI (graphical user interface) which extensively uses graphics when displaying information on the display device 45 to an operator, such as a surgeon, and which allows basic operations to be performed by means of the input device 44.

The input device 44 is a pointing device that can be operated by an operator, and sends an input signal that is in accordance with the operation to the CPU 41.

The display device 45 includes an image synthesizing circuit, a VRAM (video random access memory), a display and the like that are not shown in the drawings. The image synthesizing circuit generates synthesized data that is obtained by synthesizing character data having various parameters or the like with image data. The VRAM expands the synthesized data on the display. The display is constituted by a liquid crystal display, a CRT (cathode ray tube) display or the like, and displays images.

The IF 46 is constituted by a connector that is adapted to the parallel connection specification or the serial connection specification. The IF 46 has a function that can perform communication control according to respective standards and connect with the network N through a telephone line, to thereby connect the X-ray CT apparatus 1A to the network N.

The image processing device 12 performs logarithmic transformation processing and correction processing (pre-processing) such as sensitivity correction with respect to raw data inputted from the DAS 24 of the scanner 11 to generate projection data, and stores the projection data in a storage such as the HDD 43. The image processing device 12 also performs processing to remove scattered radiation with respect to the preprocessed projection data. The image processing device 12 removes scattered radiation on the basis of the values of the projection data within an X-ray exposure range by performing scattered radiation correction that subtracts scattered radiation that is estimated according to the size of a value of the projection data that is the target of the scattered radiation correction or of projection data adjacent to the target projection data from the projection data that is the target. The image processing device 12 generates image data based on scanning on the basis of the corrected projection data, and stores the image data in a storage such as the HDD 43 or displays the image data on the display device 45.

Figure 5:
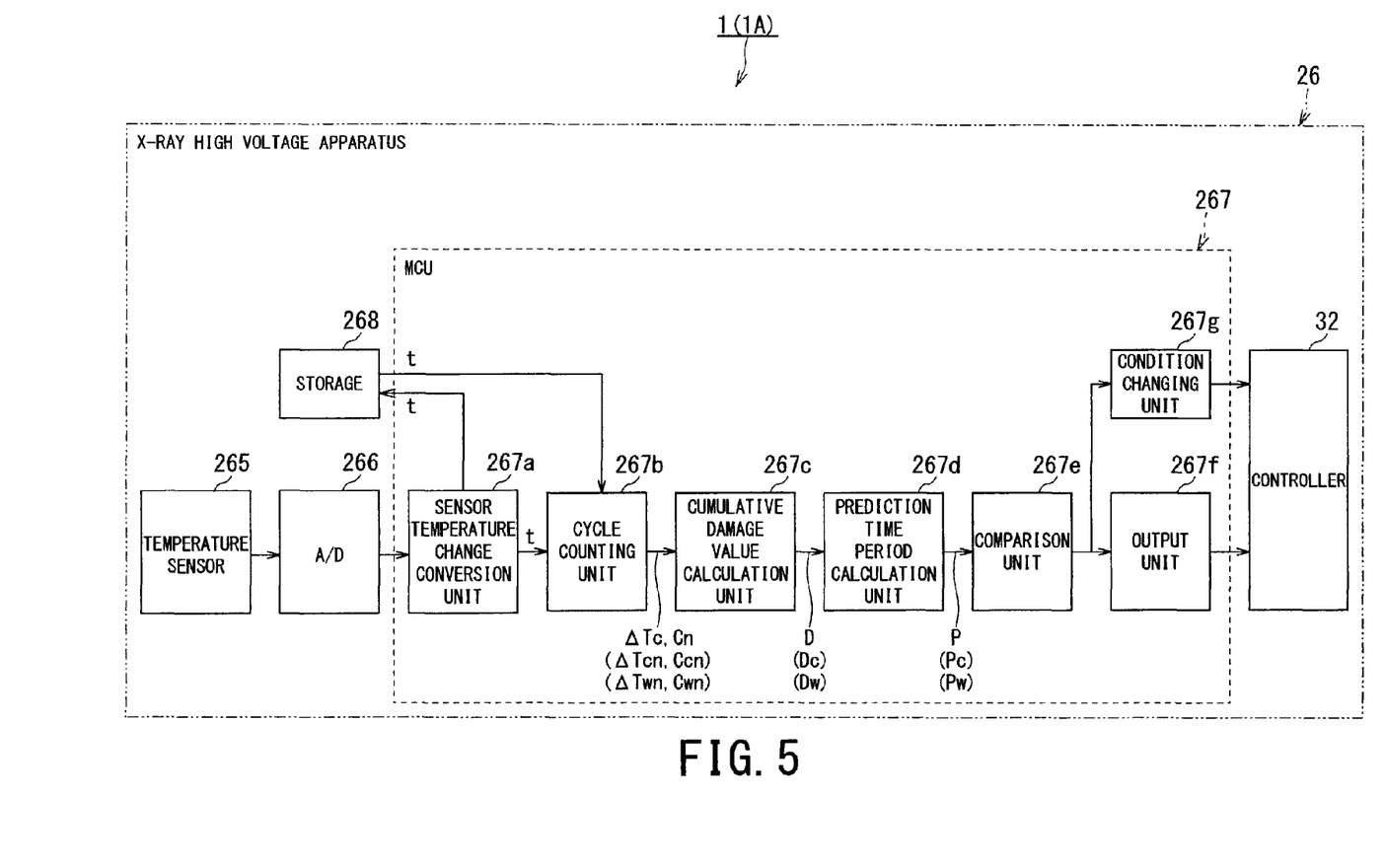
FIG. 5 is a block diagram showing a configuration and functions of the X-ray high voltage apparatus included in the X-ray CT apparatus.

FIG. 5 is a block diagram showing a configuration and functions of the X-ray high voltage apparatus included in the X-ray CT apparatus 1A.

As shown in FIG. 5, the X-ray high voltage apparatus 26 of the X-ray CT apparatus 1A includes a temperature sensor 265 (also shown in FIG. 3), an A/D (analog to digital) converter 266, an MCU (microcomputer) 267, and the storage 268.

The A/D converter 266 performs A/D conversion of a voltage at a connecting point between the resistor and thermistor that changes according to the temperature.

A sensor temperature change t, described later, that was converted by the MCU 267 is stored in the storage 268 that is a nonvolatile storage, for example, a flash memory, from which data is not erased even when the power of the X-ray high voltage apparatus 26 is turned off. By collecting the sensor temperature change t at fixed time intervals, the collected data can be stored in the storage 268 as data for sensor temperature changes t that are a plurality of sensor temperatures in time series.

By execution of a program by the MCU 267, the X-ray CT apparatus 1A functions as a sensor temperature change conversion unit 267a, a cycle counting unit 267b, a cumulative damage value calculation unit 267c, a prediction time period calculation unit 267d, a comparison unit 267e, an output unit 267f, and a condition changing unit 267g. Note that some or all of the respective portions 267a to 267g may be provided as hardware in the X-ray CT apparatus 1A.

The sensor temperature change conversion unit 267a has a function that performs processing to read a voltage that was subjected to digital conversion by the A/D converter 266, and converts the voltage to sensor temperature data based on a characteristic of the thermistor, a resistance value, and a power supply voltage, thereby acquires data for the sensor temperature change t at the position of the temperature sensor 265 provided inside or outside the power device 263.

The cycle counting unit 267b has a function that, based on the sensor temperature change t converted by the sensor temperature change conversion unit 267a or the sensor temperature change t stored in the storage 268, calculates data for the temperature change T after conversion is performed by conversion processing based on a physical model of the power device 263 (shown in FIG. 2), and calculates a cycle count Cn (C1, C2, . . . ) with respect to each temperature amplitude $\Delta Tn$ ($\Delta T1$, $\Delta T2$, . . . ) of a plurality of temperature amplitudes using a cycle counting algorithm that takes a temperature change as an amplitude. A rainflow-counting algorithm, a peak count method, a level-crossing count method, a mean crossing count method, a range count method, and a range pair count method may be mentioned as examples of the cycle counting algorithm. In this case, the rainflow-counting algorithm that is a typical method for estimating fatigue life is adopted as the cycle counting algorithm.

On the basis of the sensor temperature change t, the cycle counting unit 267b performs conversion processing based on a physical model and calculates a temperature change of the power device 263 as data of a temperature change Tc inside the case 266. Subsequently, using a cycle counting algorithm that takes a temperature change as an amplitude, the cycle counting unit 267b calculates a cycle count Ccn (Cc1, Cc2, . . . ) for each case temperature amplitude $\Delta Tcn$ ($\Delta Tc1$, $\Delta Tc2$, . . . ) of a plurality of case temperature amplitudes. Furthermore, on the basis of the sensor temperature change t, the cycle counting unit 267b performs conversion processing based on the physical model and calculates data for a temperature change Tw of the wire 264 (the joint portion with the power device 263) (shown in FIG. 2). Subsequently, using a cycle counting algorithm that takes a temperature change as an amplitude, the cycle counting unit 267b calculates a cycle count Cwn (Cw1, Cw2, . . . ) for each wire temperature amplitude $\Delta Twn$ ($\Delta Tw1$, $\Delta Tw2$, . . . ) of a plurality of wire temperature amplitudes. The cycle counting unit 267b calculates at least one of a cycle count Cpn of a pn of the case temperature amplitude $\Delta Tc$ and a junction temperature range $\Delta Tj$ and a cycle count Cwn of the wire temperature amplitude $\Delta Twn$.

Figure 6:
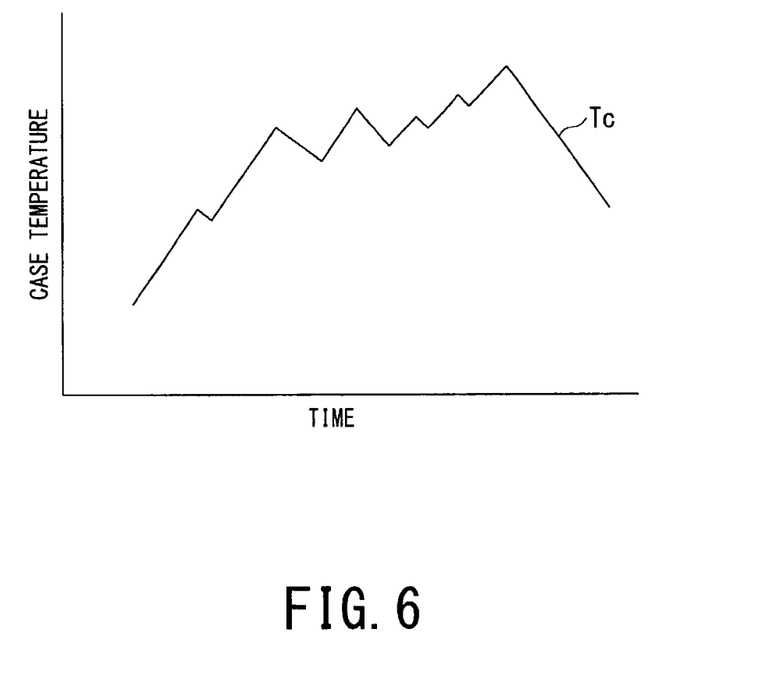
FIG. 6 is a diagram showing an example of data for a case temperature change.
Figure 7:
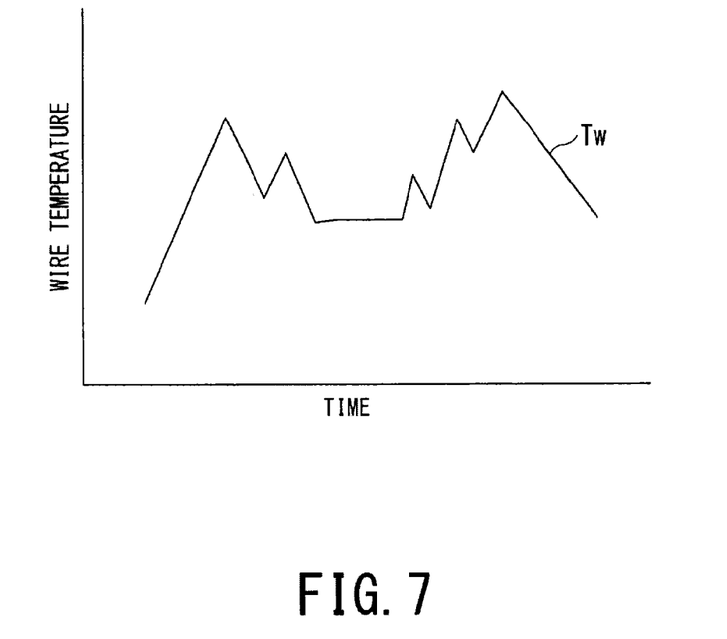
FIG. 7 is a diagram showing an example of data for a wire temperature change.

FIG. 6 is a diagram showing an example of data for the case temperature change Tc. FIG. 7 is a diagram showing an example of data for the wire temperature change Tw.

As shown in FIG. 6 and FIG. 7, in the case of the X-ray CT apparatus 1A, because the number of CT scans or the number of X-ray radiographs varies according to the conditions of use such as the diagnostic purpose and the physique of the patient, the case temperature amplitudes and the wire temperature amplitudes undergo large changes and do not change in a simple manner.

Returning to the description of FIG. 5, the cycle counting unit 267b executes a parameter survey relating to the load and cooling performance (surface coefficient of heat-transfer), and previously generates a conversion model for converting to the case temperature change Tc and the wire temperature change Tw, respectively, based on the sensor temperature change t of the temperature sensor 265 (thermistor). Specifically, the case temperature change Tc is obtained by referring to the respective temperatures for the sensor temperature change t in a table in which temperatures inside the case 266 (shown in FIG. 4) that covers the power device 263 are associated with actually measured temperatures. Further, the wire temperature change Tw is obtained by referring to the respective temperatures for the sensor temperature change t in a table in which temperature data for the wire 264 (shown in FIG. 3 and FIG. 4) that is bonded to the power device 263 is associated with data of actually measured temperatures.

The cumulative damage value calculation unit 267c has a function that, based on the cycle count C (Ccn and Cwn) of each temperature amplitude ΔTn (ΔTcn and ΔTwn) calculated by the cycle counting unit 267b, calculates fatigue damage in accordance with a linear cumulative damage rule (minor rule), and calculates a cumulative damage value D (a power device cumulative damage value Dc and a wire cumulative damage value Dw) as linear sums thereof.

The prediction time period calculation unit 267d has a function that, based on the cumulative damage value D (Dc and Dw) calculated by the cumulative damage value calculation unit 267c, calculates a prediction time period P (a case prediction time period Pc and a wire prediction time period Pw) until breakdown (failure) of the power device 263 at which the cumulative damage value D (Dc and Dw) becomes "1". The prediction time period calculation unit 267d calculates a cycle count with respect to each temperature amplitude of a plurality of temperature amplitudes per unit time, and calculates a time period until the cumulative damage value becomes "1". Note that in a case where the operational status of the power device 263 is decided in cycle units, the prediction time period calculation unit 267d can also calculate a cycle count for each temperature amplitude per cycle, and calculate the number of cycles until the cumulative damage value becomes "1".

Figure 8:
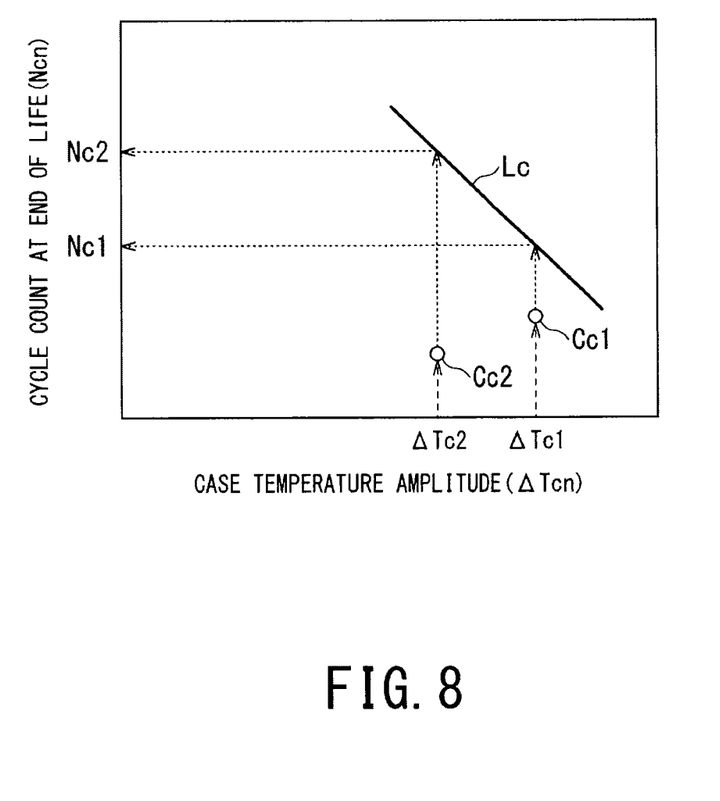
FIG. 8 is a diagram for describing a method of calculating a power device prediction time period.
Figure 9:
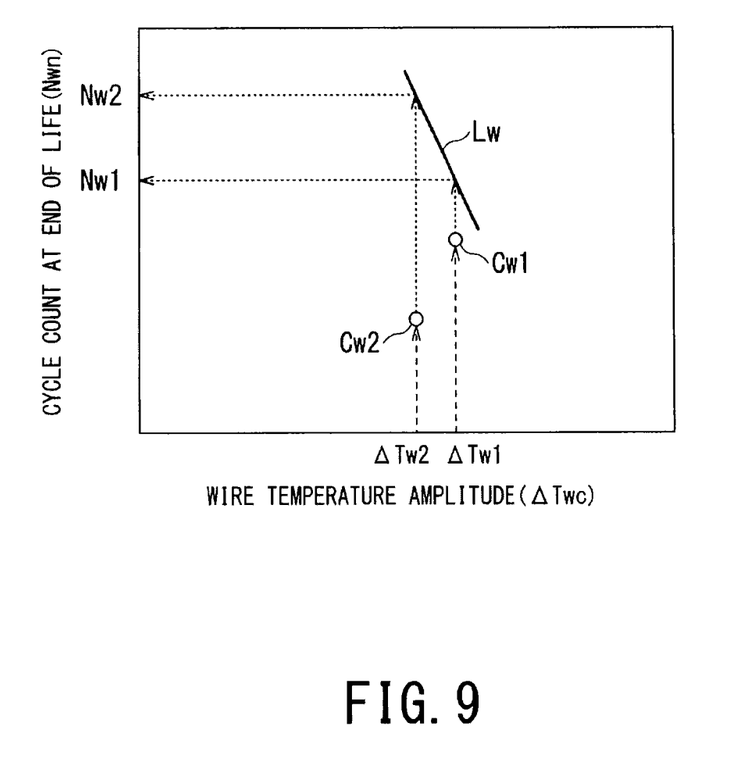
FIG. 9 is a diagram for describing a method of calculating a wire prediction time period.

FIG. 8 is a diagram for describing a method of calculating the power device prediction time period Pc. FIG. 9 is a diagram for describing a method of calculating a wire prediction time period Pw.

Thermal fatigue life prediction lines (S-N curves) Lc and Lw that are based on a response surface methodology are shown in FIG. 8 and FIG. 9, respectively. For example, the thermal fatigue life prediction lines Lc and Lw are calculated for the inside of the case 266 covering the power device 263 and for the wire 264, respectively, based on a load "on" time, a load "off" time, a calorific value, an environmental temperature and the cooling performance of the power device 263 (shown in FIG. 2).

As shown in FIG. 8, assuming that the respective case temperature amplitudes ΔTcn (ΔTc1, ΔTc2, . . . ) calculated by the cycle counting unit 267b (shown in FIG. 5) occur, a cycle count Ncn (Nc1, Nc2, . . . ) until a breakage occurs in the case of each case temperature amplitude ΔTcn can be read from the thermal fatigue life prediction line Lc. Further, based on each cycle count Ncn (Nc1, Nc2, . . . ) and the actual cycle count Ccn (Cc1, Cc2, . . . ) of each case temperature amplitude ΔTcn, the degree of cumulative damage at each case temperature amplitude ΔTcn is calculated as Ccn/Ncn (Cc1/Nc1, Cc2/Nc2, . . . ). According to the cumulative damage rule, as shown in equation (1) below, the sum of these individual degrees of cumulative damage is taken as an overall cumulative damage value Dc. It is assumed that fatigue damage occurs when the cumulative damage value Dc becomes "1".

$$Dc = \frac{Cc1}{Nc1} + \frac{Cc2}{Nc2} + \ldots = \sum \frac{Ccn}{Ncn} \quad (1)$$

As shown in FIG. 9, assuming that the respective wire temperature amplitudes ΔTwn (ΔTw1, ΔTw2, . . . ) calculated by the cycle counting unit 267b (shown in FIG. 5) occur, a cycle count Nwn (Nw1, Nw2, . . . ) until a breakage occurs in the case of each wire temperature amplitude ΔTwn can be read from the thermal fatigue life prediction line Lw. Further, based on each cycle count Nwn (Nw1, Nw2, . . . ) and the actual cycle count Cwn (Cw1, Cw2, . . . ) of each wire temperature amplitude ΔTwn, the degree of cumulative damage at each wire temperature amplitude ΔTwn is calculated as Cwn/Nwn (Cw1/Nw1, Ccw2/Nw2, . . . ). According to the cumulative damage rule, as shown in equation (2) below, the sum of these individual degrees of cumulative damage is taken as an overall cumulative damage value Dw. It is assumed that fatigue damage occurs when the cumulative damage value Dw becomes "1".

$$Dw = \frac{Cw1}{Nw1} + \frac{Cw2}{Nw2} + \ldots = \sum \frac{Cwn}{Nwn} \quad (2)$$

Returning to the description of FIG. 5, the comparison unit 267e has a function that compares the prediction time period P (Pc and Pw) calculated by the prediction time period calculation unit 267d and a previously set threshold value.

The output unit 267f has a function that, in a case where it is determined as a result of a comparison by the comparison unit 267e that the prediction time period P (Pc and Pw) are less than (less than or equal to) the threshold value, outputs a signal to that effect. The output unit 267f may be configured so that, when it is determined that either one of the case prediction time period Pc and the wire prediction time period Pw is less than the threshold value or that both of the case prediction time period Pc and the wire prediction time period Pw are less than the threshold value, the output unit 267f outputs a signal to that effect. The output unit 267f notifies the display device 45 or the like via the controller 32 to the effect that a prediction time period is less than the threshold value, or transmits a signal to an external apparatus (not shown in the drawings) of a service center or the like through the controller 32, the IF 46 and the network N.

The condition changing unit 267g has a function that, in a case where it is determined as a result of the comparison by the comparison unit 267e that the prediction time period P (Pc and Pw) are less than (less than or equal to) the threshold value, changes an operating condition of the power device 263 of the X-ray high voltage apparatus 26 through the controller 32. For example, the condition changing unit 267g changes an abnormal current threshold value of the power device 263 or a module (not shown in the drawings) including a plurality of the power devices 263, increases the cooling performance (the fan speed or the like) of the power device 263 or the module, or switches the operating module to a standby module.

According to the medical apparatus 1 according to the present embodiment, the life of the power device 263 can be predicted from the viewpoint of a heat cycle life that causes cracking at the solder joint portion S1 (shown in FIG. 4) or a power cycle life that causes cracking at the solder joint portion S2 (shown in FIG. 4). According to the medical apparatus 1 and the X-ray high voltage apparatus 26 according to the present embodiment, since a situation in which a failure of the power device 263 suddenly occurs during a radiography operation can be avoided by predicting the life of the power device 263, it is not necessary to re-perform a radiography operation, and therefore unnecessary radiation exposure of the patient O can be avoided.

In addition, according to the medical apparatus 1 and the X-ray high voltage apparatus 26 according to the present embodiment, an operator or a person involved in servicing the medical apparatus 1 and the X-ray high voltage apparatus 26 can be notified before a failure of the power device 26 occurs.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A medical apparatus, comprising:
   an X-ray tube configured to emit an X-ray;
   an X-ray high voltage apparatus configured to apply X-ray high voltage to the X-ray tube;
   a power device;
   a temperature sensor configured to detect a temperature while the X-ray high voltage apparatus applies the high voltage to the X-ray tube;
   processing circuitry configured to
      refer, using the detected temperature, to a table in which at least one of a case temperature for inside a case covering the power device and a wire temperature for a wire bonded to the power device is associated with data of actually detected temperatures, and obtain at least one of the case temperature and the wire temperature; and
      calculate a prediction time period until a failure of the power device based on the obtained temperature data,
   wherein the processing circuitry is further configured to
      calculate a cycle count for each temperature amplitude of a plurality of temperature amplitudes using a rainflow counting algorithm that takes as the temperature amplitude a temperature change from one temperature peak value to another temperature peak value of the obtained at least one of the case temperature and the wire temperature,
      calculate a cumulative damage value based on the plurality of temperature amplitudes and cycle counts corresponding to the plurality of temperature amplitudes, respectively, and
      calculate the prediction time period based on the cumulative damage value.

2. The medical apparatus according to claim 1, wherein the processing circuitry is further configured to:
   compare the prediction time period and a threshold value; and
   output when the prediction time period is less than the threshold value, information to that effect.

3. The medical apparatus according to claim 2, wherein the processing circuitry is further configured to cause a display device to display information indicating that the prediction time period is less than the threshold value, or to transmit such information to an external apparatus through a communication line.

4. The medical apparatus according to claim 1, wherein the processing circuitry is further configured to:
   compare the prediction time period and a threshold value; and
   change an operating condition of the power device when the prediction time period is less than the threshold value.

5. The medical apparatus according to claim 1, wherein the processing circuitry is further configured to calculate the cumulative damage value using a rainflow-counting algorithm as the cycle counting algorithm.

6. An X-ray high voltage apparatus, comprising:
   a power device;
   a temperature sensor configured to detect a temperature while the X-ray high voltage apparatus applies a high voltage to an X-ray tube;
   processing circuitry configured to
      refer, using the detected temperature data obtained by the temperature sensor, to a table in which at least one of a case temperature for inside a case covering the power device and a wire temperature for a wire bonded to the power device is associated with data of actually detected temperatures, and obtain at least one of the case temperature and the wire temperature; and
      calculate a prediction time period until a failure of the power device based on the obtained temperature data,
   wherein the processing circuitry is further configured to
      calculate a cycle count for each temperature amplitude of a plurality of temperature amplitudes using a rainflow counting algorithm that takes as the temperature amplitude a temperature change from one temperature peak value to another temperature peak value of the obtained at least one of the case temperature and the wire temperature,
      calculate a cumulative damage value based on the plurality of temperature amplitudes and cycle counts corresponding to the plurality of temperature amplitudes, respectively and
      calculate the prediction time period based on the cumulative damage value.

7. The X-ray high voltage apparatus according to claim 6, wherein the processing circuitry is further configured to:
   compare the prediction time period and a threshold value; and output when the prediction time period is less than the threshold value, information to that effect.

8. The X-ray high voltage apparatus according to claim 7, wherein
the processing circuitry is further configured to cause a display device to display information indicating that the prediction time period is less than the threshold value, or to transmit such information to an external apparatus through a communication line.

9. The X-ray high voltage apparatus according to claim 6, wherein the processing circuitry is further configured to:
compare the prediction time period and a threshold value; and
change an operating condition of the power device when the prediction time period is less than the threshold value.

10. The X-ray high voltage apparatus according to claim 6, wherein the processing circuitry is further configured to calculate the cumulative damage value using a rainflow-counting algorithm as the cycle counting algorithm.

* * * * *